(12) United States Patent
Pyun et al.

(10) Patent No.: US 9,879,038 B2
(45) Date of Patent: Jan. 30, 2018

(54) SALT OF TENOFOVIR DISOPROXIL

(71) Applicant: JW Pharmaceutical Corporation, Seoul (KR)

(72) Inventors: Do-Kyu Pyun, Hwaseong-si (KR); Won-Kyoung Lee, Hwaseong-si (KR); Su-Ha Park, Seoul (KR)

(73) Assignee: JW PHARMACEUTICAL CORPORATION, Seoul (KR)

( * ) Notice: Subject to any disclaimer, the term of this patent is extended or adjusted under 35 U.S.C. 154(b) by 0 days.

(21) Appl. No.: 15/325,988

(22) PCT Filed: Jul. 9, 2015

(86) PCT No.: PCT/KR2015/007130
§ 371 (c)(1),
(2) Date: Jan. 12, 2017

(87) PCT Pub. No.: WO2016/010305
PCT Pub. Date: Jan. 21, 2016

(65) Prior Publication Data
US 2017/0152276 A1    Jun. 1, 2017

(30) Foreign Application Priority Data
Jul. 18, 2014 (KR) .................. 10-2014-0091262

(51) Int. Cl.
*C07F 9/6561* (2006.01)
*C07C 309/05* (2006.01)

(52) U.S. Cl.
CPC ........ *C07F 9/65616* (2013.01); *C07C 309/05* (2013.01)

(58) Field of Classification Search
CPC .................... C07F 9/65616; C07C 309/05
See application file for complete search history.

(56) References Cited

U.S. PATENT DOCUMENTS

2009/0176983 A1* 7/2009 Dova .................. A61K 31/675
544/242

FOREIGN PATENT DOCUMENTS

| CN | 101 574 356 A | | 11/2009 |
|---|---|---|---|
| JP | 2011-506374 A | | 3/2011 |
| KR | 10-2006-0127939 | | 12/2006 |
| KR | 10-2009-0098995 | | 9/2009 |
| KR | 10-2015-0025993 | | 3/2015 |
| WO | WO 2006007448 | * | 1/2006 |
| WO | WO 2009/074351 A2 | | 6/2009 |
| WO | WO 2009/130437 A1 | | 10/2009 |
| WO | WO 2010/026603 A2 | | 3/2010 |
| WO | WO 2012/137227 A2 | | 10/2012 |
| WO | WO 2014/035064 A1 | | 3/2014 |

OTHER PUBLICATIONS

International Search Report in connection with PCT International Application No. PCT/KR2015/007130.
Extended European Search Report dated Jun. 6, 2017 in connection with European Patent Application No. 15822313.1.

* cited by examiner

*Primary Examiner* — Shirley V Gembeh
(74) *Attorney, Agent, or Firm* — John P. White; Cooper & Dunham LLP

(57) ABSTRACT

Disclosed is a novel tenofovir disoproxil edisylate salt having the structure of Chemical Formula 1.

9 Claims, 11 Drawing Sheets

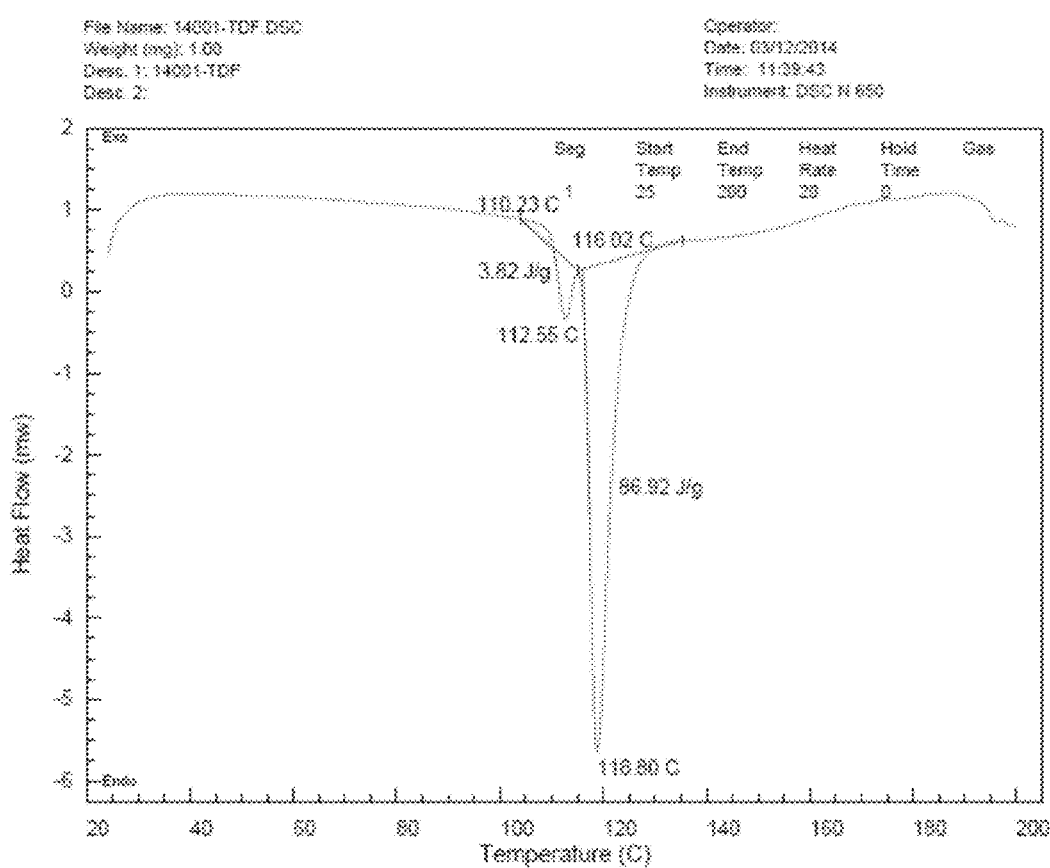

SALT OF TENOFOVIR DISOPROXIL

CROSS-REFERENCE TO RELATED APPLICATIONS

This application is a §371 national stage of PCT International Application No. PCT/KR2015/007130, filed Jul. 9, 2015, claiming priority of Korean Patent Application No. KR 10-2014-0091262, filed Jul. 18, 2014, the content of each of which is hereby incorporated by reference into the application.

TECHNICAL FIELD

The present invention relates to a novel salt of tenofovir disoproxil.

BACKGROUND ART

Tenofovir disoproxil fumarate (TDF) salt is a compound having the chemical name of 9-[2-(R)-[[bis[[(isopropoxycarbonyl)oxy]methoxy]phosphinoyl]methoxy]propyl]adenine fumaric acid (1:1), is a prodrug to be hydrolyzed upon absorption, and is a phosphonomethoxy nucleotide analogue useful in the treatment of HIV-1 infection and chronic hepatitis B.

TDF was approved as a therapeutic agent for the treatment of AIDS, and was then approved as a therapeutic agent for the treatment of hepatitis B by the U.S. Food and Drug Administration. Tenofovir, which is an active metabolite of TDF, has a high ability to inhibit hepatitis B virus DNA in patients resistant to lamivudine (Zeffix), and is an antiviral agent belonging to Pregnancy category B (which are drugs found to have no fetal risk in animal studies) for assessment of the risk of fetal injury due to the pharmaceutical, as categorized by the U.S. Food and Drug Administration (FDA).

However, ensuring the physicochemical stability of tenofovir is known to be difficult. As reported in published literature (Pharmaceutical Research, 2001, 18, 234-237; Pharmaceutical Research, 2000, 17, 1098-1103), tenofovir disoproxil is hydrolyzed in the presence of water to give formaldehyde, which is then subjected to a condensation reaction with the N6-amine group of tenofovir disoproxil, thus producing a tenofovir disoproxil dimer as an impurity.

Generally, in order to expect consistent effects of medicines, the amount of an active ingredient has to be prevented from decomposition not only immediately after the manufacture of medicines but also during the storage thereof, and furthermore, an increase in the amounts of impurities or related substances, which are degradation products of the active ingredient during the same periods, has to be inhibited. Hence, preventing impurities from being incorporated into medicines is regarded as very important in terms of quality control of medicines.

As for the official compendium regulations of individual countries on purity testing, the Korean Pharmacopoeia has a separate regulation for related substances under the purity test section, and the U.S. Pharmacopoeia has regulations for "ordinary impurities", in which the sum of related substances is set to 2.0% or less unless otherwise specified, or in which the amounts of related substances are regulated based on related compounds and chromatographic purity under each article of pharmaceutical drugs. Furthermore, the European and British Pharmacopoeias regulate related substances, and the Japanese Pharmacopoeia regulates related substances and amounts thereof in purity testing.

Therefore, the present inventors have studied novel salts able to minimize the generation of related substances even upon long-term storage and maximize solubility while exhibiting physicochemical properties equal or superior to those of conventional tenofovir disoproxil fumarate salt, leading to the development of novel tenofovir disoproxil edisylate salt using edisylate.

DISCLOSURE

Technical Problem

Accordingly, the present invention is intended to provide a novel tenofovir disoproxil salt compound, which has physicochemical properties equal or superior to those of tenofovir disoproxil fumarate salt, may minimize the generation of related substances even upon long-term storage, and may maximize solubility.

Technical Solution

The present invention provides tenofovir disoproxil edisylate salt represented by Chemical Formula 1 below.

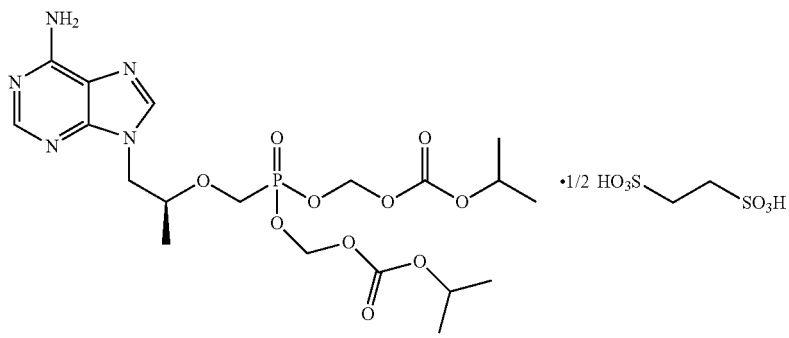

<Chemical Formula 1>

9-[(R)-2-[[bis[[(isopropoxycarbonyl)oxy]methoxy]phosphinyl]methoxy]propyl]adenine hemiedisylate In an embodiment of the present invention, the compound of Chemical Formula 1 may be a hemi-edisylate salt in which tenofovir disoproxil and edisylate salt are bound at a molar ratio of 1:0.5.

In another embodiment of the present invention, the compound of Chemical Formula 1 may be tenofovir disoproxil edisylate salt having the following $^1$H nuclear magnetic resonance (NMR) peaks: $^1$H NMR (500 MHz, DMSO) 8.44 (s, 1H), 8.33 (s, 1H), 5.54-5.45 (m, 4H), 4.82-4.77 (m, 2H), 4.38-4.35 (dd, 1H), 4.25-4.4.21 (dd, 1H), 4.01-3.90 (m, 3H), 2.67 (s, 2H), 1.23-1.22 (d, 12H), and 1.09-1.08 (d, 3H) ppm.

In still another embodiment of the present invention, the compound of Chemical Formula 1 may have the following X-ray powder diffraction peak values: 4.14°, 10.40°, 11.67°, 12.64°, 12.90°, 13.24°, 15.64°, 16.30°, 16.86°, 18.69°, 18.74°, 19.19°, 19.82°, 20.74°, 21.36°, 21.89°, 22.46°, 23.19°, 23.72°, 24.88°, 25.56°, 26.21°, and 27.04°.

In addition, the present invention provides a crystalline form of tenofovir disoproxil edisylate salt, having the X-ray powder diffraction peak values shown in FIG. 5: 3.32°, 4.18°, 5.13°, 7.31°, 8.59°, 10.01°, 10.42°, 10.97°, 11.56°, 12.64°, 12.95°, 13.25°, 14.67°, 15.53°, 16.39°, 17.33°, 18.15°, 18.75°, 19.28°, 19.93°, 20.44°, 20.81°, 21.37°, 22.03°, 22.49°, 22.84°, 23.28°, 23.75°, 24.66°, 25.00°, 25.65°, 26.36°, 27.1°, 27.76°, 28.16°, 28.79°, 30.31°, and 31.17°.

The present invention provides a crystalline form of tenofovir disoproxil edisylate salt, having the X-ray powder diffraction peak values shown in FIG. 6.

The present invention provides a pharmaceutical composition for the prevention or treatment of a disease associated with viral infection, the composition comprising a therapeutically effective amount of tenofovir disoproxil edisylate salt.

In an embodiment of the present invention, the virus may include HIV, HBV, CMV, HSV-1, HSV-2, or human herpes virus.

In an embodiment of the present invention, the pharmaceutical composition may be provided in a dosage form of a tablet, a capsule, a powder, a granule, a dropping pill, a pulvis, a bolus, a tincture or a cataplasm.

The present invention provides a method of preventing or treating viral infection in a mammal, comprising administering a therapeutically effective amount of tenofovir disoproxil edisylate salt to a mammal in need thereof.

In an embodiment of the present invention, the virus may include HIV, HBV, CMV, HSV-1, HSV-2, or human herpes virus.

Advantageous Effects

According to the present invention, tenofovir disoproxil edisylate salt can minimize the generation of related substances over time compared to tenofovir disoproxil fumarate, whereby the production of impurities can be significantly decreased during the storage of products containing the salt compound of the invention, thus increasing the stability of drugs and obviating the need to perform additional studies on toxic effects. The salt compound of the present invention can be greatly improved in stability despite changes in pH, moisture resistance and solubility and can exhibit excellent physicochemical properties, and can thus be used as an active ingredient of a pharmaceutical composition for the treatment of HIV-1 infection and chronic hepatitis B, together with a pharmaceutically acceptable carrier. Furthermore, the salt compound of the present invention possesses very high solubility even upon changes in pH compared to other tenofovir disoproxil salts (e.g. orotate salt, aspartate salt, hippurate salt and the like).

Moreover, even when the tenofovir disoproxil edisylate of the present invention is prepared using a simple process, much purer tenofovir disoproxil can be obtained during the synthesis of an acid addition salt.

DESCRIPTION OF DRAWINGS

FIG. 7a shows the measurement values of differential scanning calorimetry (DSC) of tenofovir disoproxil fumarate;

BEST MODE

Hereinafter, a detailed description will be given of the present invention.

An aspect of the present invention addresses tenofovir disoproxil edisylate represented by Chemical Formula 1 below.

<Chemical Formula 1>

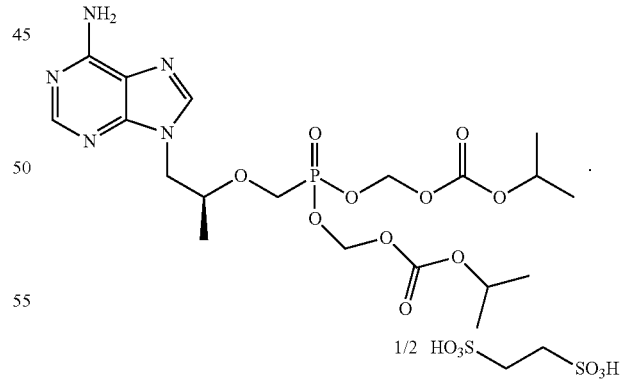

9-[(R)-2-[[bis[[(isopropoxycarbonyl)oxy]methoxy] phosphinyl]methoxy]propyl]adenine hemiedisylate In an embodiment of the present invention, the compound of Chemical Formula 1 is preferably a hemi-edisylate salt in which tenofovir disoproxil and edisylate salt are bound at a molar ratio of 1:0.5.

In another embodiment of the present invention, the compound of Chemical Formula 1 may be tenofovir disoproxil edisylate salt having the following $^1$H NMR peaks: $^1$H NMR (500 MHz, DMSO) 8.44 (s, 1H), 8.33 (s, 1H), 5.54-5.45 (m, 4H), 4.82-4.77 (m, 2H), 4.38-4.35 (dd, 1H), 4.25-4.4.21 (dd, 1H), 4.01-3.90 (m, 3H), 2.67 (s, 2H), 1.23-1.22 (d, 12H), and 1.09-1.08 (d, 3H) ppm.

In still another embodiment of the present invention, the compound of Chemical Formula 1 may have the following X-ray powder diffraction peak values: 4.14°, 10.40°, 11.67°, 12.64°, 12.90°, 13.24°, 15.64°, 16.30°, 16.86°, 18.69°, 18.74°, 19.19°, 19.82°, 20.74°, 21.36°, 21.89°, 22.46°, 23.19°, 23.72°, 24.88°, 25.56°, 26.21°, and 27.04°.

Figure 5:
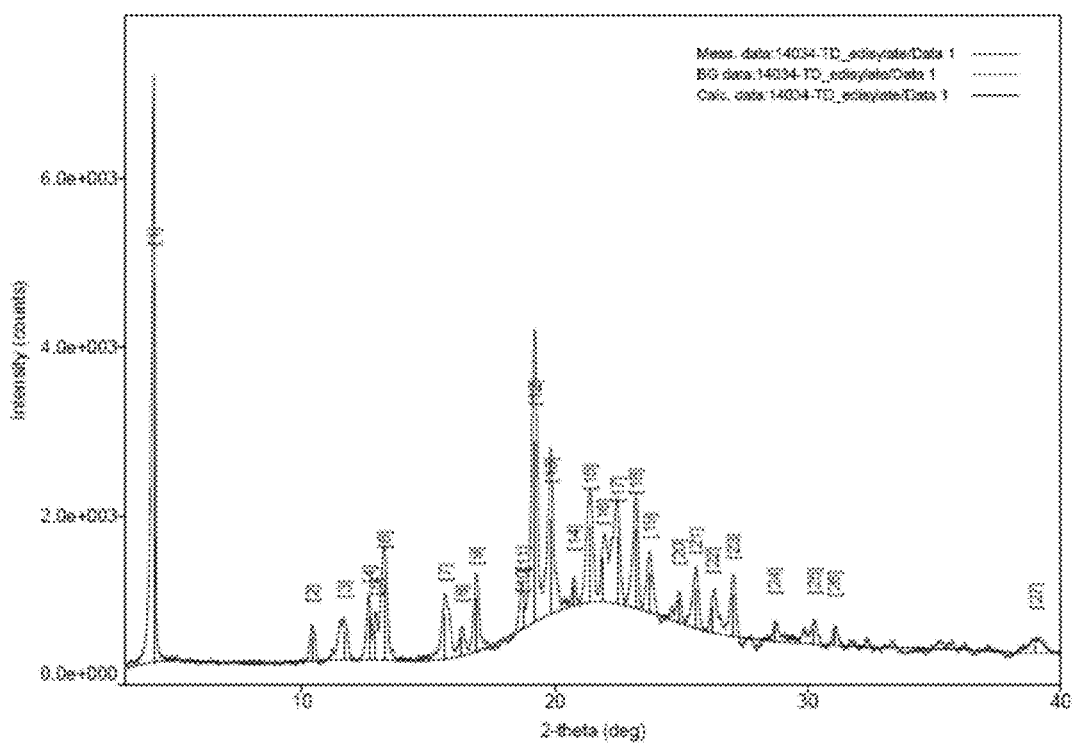
FIG. 5 shows the results of X-ray diffraction analysis of tenofovir disoproxil hemi-edisylate A.

In addition, the present invention addresses a crystalline form of tenofovir disoproxil edisylate salt, having the X-ray powder diffraction peak values shown in FIG. 5: 3.32°, 4.18°, 5.13°, 7.31°, 8.59°, 10.01°, 10.42°, 10.97°, 11.56°, 12.64°, 12.95°, 13.25°, 14.67°, 15.53°, 16.39°, 17.33°, 18.15°, 18.75°, 19.28°, 19.93°, 20.44°, 20.81°, 21.37°, 22.03°, 22.49°, 22.84°, 23.28°, 23.75°, 24.66°, 25.00°, 25.65°, 26.36°, 27.1°, 27.76°, 28.16°, 28.79°, 30.31°, and 31.17°.

Figure 6:
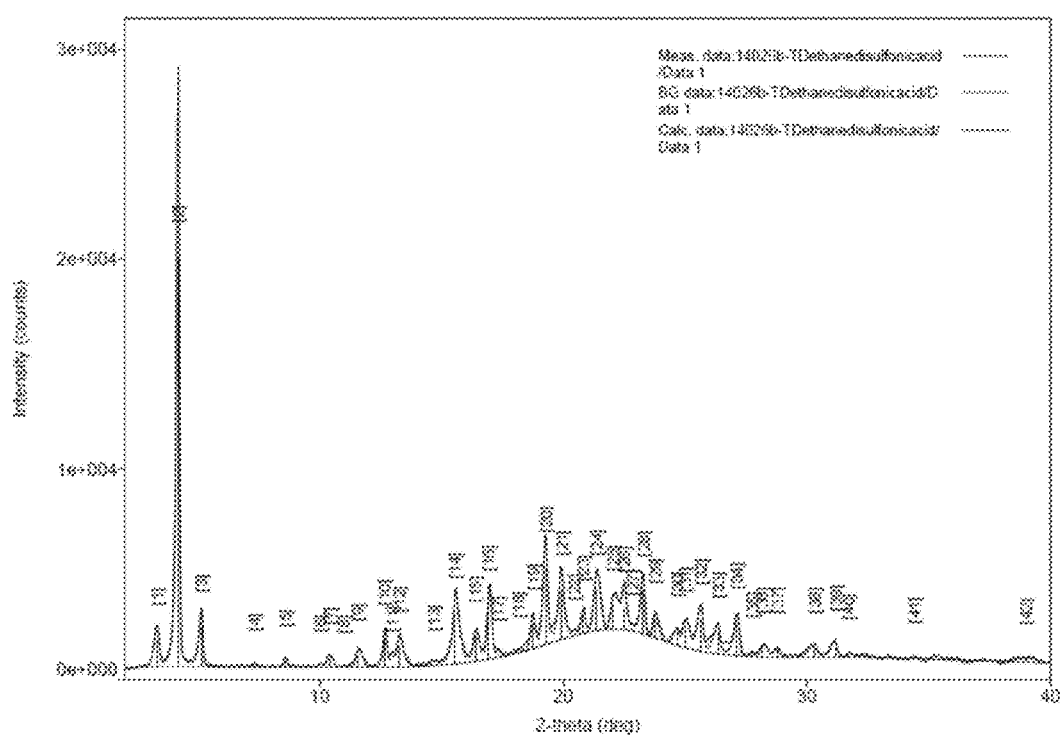
FIG. 6 shows the results of X-ray diffraction analysis of tenofovir disoproxil hemi-edisylate B.

Also, the present invention addresses a crystalline form of tenofovir disoproxil edisylate salt, having the X-ray powder diffraction peak values shown in FIG. 6.

Another aspect of the present invention addresses a pharmaceutical composition for the prevention or treatment of a disease associated with viral infection, the composition comprising a therapeutically effective amount of tenofovir disoproxil edisylate salt.

In an embodiment of the present invention, the virus may include HIV, HBV, CMV, HSV-1, HSV-2 or human herpes virus, and the pharmaceutical composition of the invention may be particularly useful in the treatment of HIV-1 infection and chronic hepatitis B.

The pharmaceutical composition of the present invention may comprise, in addition to the therapeutically effective amount of tenofovir disoproxil edisylate, a pharmaceutically acceptable excipient. As necessary, the pharmaceutical composition may further comprise an additional antiviral agent and an additional therapeutic ingredient or assistant ingredient, such as an immune stimulant, a liver protectant, and L-carnitine and salts thereof.

The pharmaceutically acceptable excipient may include, but is not limited to, any one or more selected from among an adhesive agent, a diluent, a disintegrant, a preservative, a dispersant, a glidant (a release agent), and a lubricant.

Typically, the pharmaceutical composition of the present invention may be administered orally, intrarectally, intravaginally, intranasally, topically (e.g. intraocularly, intraorally, and sublingually) or parenterally (e.g. subcutaneously, intramuscularly, intravenously, intradermally, intraspinally or epidurally). Oral administration is preferable.

The pharmaceutical composition of the present invention may be preferably provided in a dosage form of a tablet, a capsule, a powder, a granule, a dropping pill, a pulvis, a bolus, a tincture or a cataplasm. The tablet is preferably provided in the form of a typical tablet, a coated tablet, a dispersible tablet, an effervescent tablet, a sustained-release tablet, a controlled-release tablet, or an enteric-coated tablet. The capsule is preferably provided in the form of a typical capsule, a sustained-release capsule, a controlled-release capsule, or an enteric-coated capsule.

When the pharmaceutical composition of the invention is a tablet or a capsule, the amount of tenofdvir disoproxil edisylate salt, serving as an active ingredient, in a unit dosage form may vary depending on a variety of factors such as symptoms and age. Generally, a single dose of the active ingredient, when orally administered, falls in the range of 5 mg to 300 mg, and preferably 5 mg to 150 mg. Also, the tablet or capsule may further comprise a bulking agent such as starch, sucrose, lactose, etc., an adhesive agent, such as water, alcohol, polyvinyl pyrrolidone, pregelatinized starch, etc., a disintegrant, such as microcrystalline cellulose, croscarmellose sodium, crosslinked polyvinyl pyrrolidone, etc., and a lubricant such as magnesium stearate, talc powder, silica, etc.

When the pharmaceutical composition of the invention is a tablet or a capsule, it preferably comprises a basic pharmaceutical carrier, including a basic carbonate and a basic hydroxide. Preferable examples of the basic carbonate are calcium carbonate, magnetic carbonate, zinc carbonate, ferrous carbonate, or aluminum carbonate. Preferable examples of the basic hydroxide are magnesium hydroxide, calcium hydroxide, aluminum hydroxide, or ferrous hydroxide.

When the pharmaceutical composition of the invention is a dispersible tablet, a disintegrant is selectively present in an amount of about 0.5 to 60% so as to realize rapid disintegration.

The dosage form of the pharmaceutical composition of the invention may be a sterile powder for injection or an injection solution. The dosage form may be administered by injection.

Still another aspect of the present invention addresses a method of preventing or treating viral infection in a mammal, comprising administering a therapeutically effective amount of tenofovir disoproxil edisylate salt to a mammal in need thereof.

Yet another aspect of the present invention addresses the use of tenofovir disoproxil edisylate salt in the manufacture of a medicament for the prevention or treatment of a disease associated with viral infection.

In the present invention, the virus includes HIV, HBV, CMV, HSV-1, HSV-2 and human herpes virus, and preferably includes HIV or HBV. The tenofovir disoproxil edisylate salt of the invention is particularly useful in the treatment of HIV-1 infection and chronic hepatitis B.

According to the present invention, the tenofovir disoproxil edisylate salt, the crystalline form, the crystalline composition, and the pharmaceutical composition are preferably suitable for use in a warm-blooded animal, and more preferably a human.

Also, the present invention addresses a method of preparing tenofovir disoproxil edisylate salt comprising reacting tenofovir disoproxil with an edisylate dihydrate. The tenofovir disoproxil and the edisylate dihydrate are preferably reacted at a molar ratio of 1:0.5 to 1.5. More preferably, the method of preparing the tenofovir disoproxil edisylate salt comprising reacting tenofovir disoproxil with an edisylate dihydrate at a molar ratio of 1:0.5 to 0.6.

MODE FOR INVENTION

A better understanding of the present invention may be obtained via the following examples, which are set forth to illustrate, but are not to be construed as limiting the scope of the present invention and may be appropriately modified and altered by those skilled in the art within the scope of the present invention.

<Example 1> Preparation of Tenofovir Disoproxil Hemi-Edisylate 200 mL of anhydrous ethanol, 10.0 g of tenofovir disoproxil, and 1.98 g of 1,1-ethane disulfone dihydrate were placed in a 500 mL reactor, stirred at 20 to 30° C. for 1 hour, cooled to 0 to 5° C., stirred for 0.5 hour, filtered, washed with 20 mL of anhydrous ethanol, and dried under reduced pressure at 40° C. for 4 hours, thus yielding 11.2 g of white tenofovir disoproxil hemi-edisylate (purity of 99.68%).

disoproxil fumarate (Comparative Example 1: TDF) as a control group were used, and analyzed using high-performance liquid chromatography (HPLC) as set forth in the U.S. Pharmacopeia (USP). The results are shown in Table 1 below (stressed conditions: 60±2° C.).

TABLE 1

| Related substances | Relative retention time | TDF | | | | TDE | | | |
|---|---|---|---|---|---|---|---|---|---|
| | | Initial | 7 days | 14 days | 21 days | Initial | 7 days | 14 days | 21 days |
| Adenine | 0.17 | 0.01 | 0.01 | 0.01 | 0.01 | — | — | — | — |
| Tenofovir isoproxil monoester | 0.25 | 0.42 | 0.79 | 1.26 | 1.81 | 0.26 | 0.27 | 0.30 | 0.37 |
| Unspecified impurity-1 | 0.49 | — | 0.01 | 0.05 | — | — | — | — | — |
| Unspecified impurity-2 | 0.58 | 0.03 | 0.09 | 0.27 | 0.18 | — | — | — | — |
| Unspecified impurity-3 | 0.64 | 0.02 | 0.03 | 0.04 | 0.03 | — | — | — | — |
| Tenofovir disoproxil ethyl ester | 0.81 | — | — | — | — | 0.01 | 0.02 | 0.01 | 0.02 |
| Tenofovir isopropyl isoproxil | 0.82 | — | — | — | — | 0.04 | 0.04 | 0.04 | 0.04 |
| Unspecified impurity-4 | 1.10 | — | — | 0.04 | — | — | — | — | — |
| Unspecified impurity-5 | 1.24 | 0.05 | 0.21 | 0.63 | 0.21 | — | — | — | — |
| Unspecified impurity-6 | 1.30 | — | — | 0.07 | — | — | — | — | — |
| Unspecified impurity-7 | 1.71 | — | — | 0.42 | — | — | — | — | — |

Figure 1A:
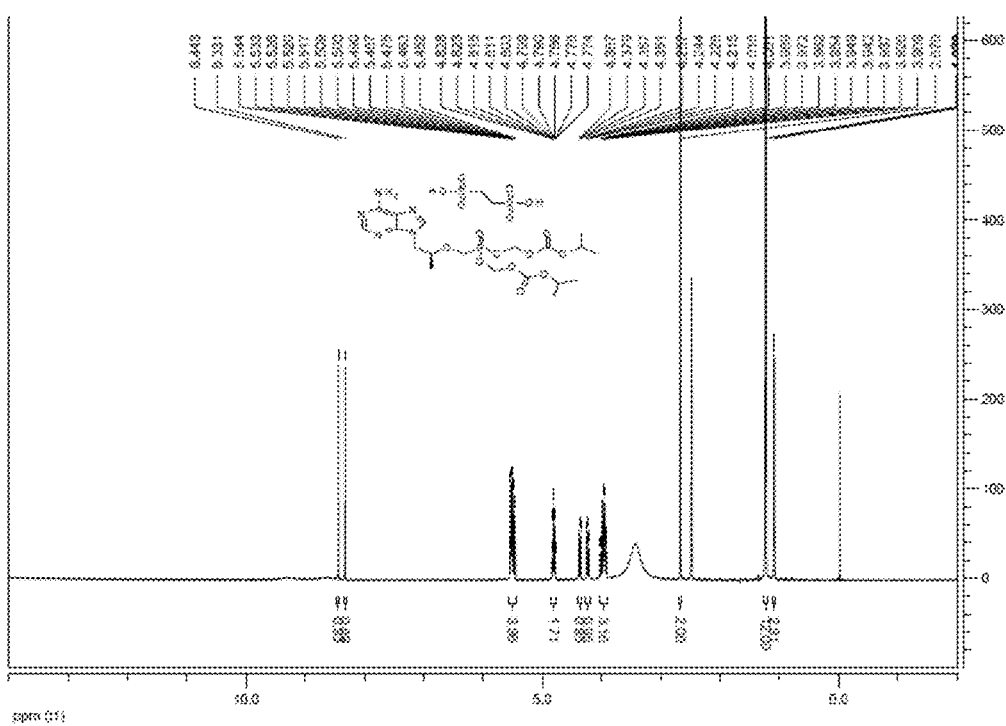
FIG. 1a shows the $^1$H NMR spectrum of tenofovir disoproxil hemi-edisylate.

$^1$H NMR (500 MHz, DMSO) 8.44 (s, 1H), 8.33 (s, 1H), 5.54-5.45 (m, 4H), 4.82-4.77 (m, 2H), 4.38-4.35 (dd, 1H), 4.25-4.4.21 (dd, 1H), 4.01-3.90 (m, 3H), 2.67 (s, 2H), 1.23-1.22 (d, 12H), 1.09-1.08 (d, 3H) ppm FIG. 1a shows the $^1$H NMR spectrum of tenofovir disoproxil hemi-edisylate.

<Comparative Example 1> Preparation of Tenofovir Disoproxil Fumarate

Tenofovir disoproxil fumarate was prepared API purchased from China.

<Comparative Example 2> Preparation of Tenofovir Disoproxil Mono-Edisylate

Tenofovir disoproxil mono-edisylate was prepared as follows.

In a 100 mL reactor, 30 mL of deionized water, 3.0 g of tenofovir disoproxil, and 1.2 g (1.1 eq.) of 1,1-ethane disulfone dihydrate were placed and stirred at 20 to 30° C. for 1 hour. After the termination of the reaction, the reaction product was concentrated to remove deionized water, added with 30 mL of toluene, and concentrated again to thus remove remaining deionized water.

The concentrated residue was dissolved in 6 mL of methanol at room temperature, stirred for 30 min together with 6 mL of isopropyl ether, crystallized, filtered, and dried under reduced pressure at 40° C. for 4 hours, thus yielding 3.4 g of white tenofovir disoproxil mono-edisylate (purity of 97.51%).

Figure 1B:
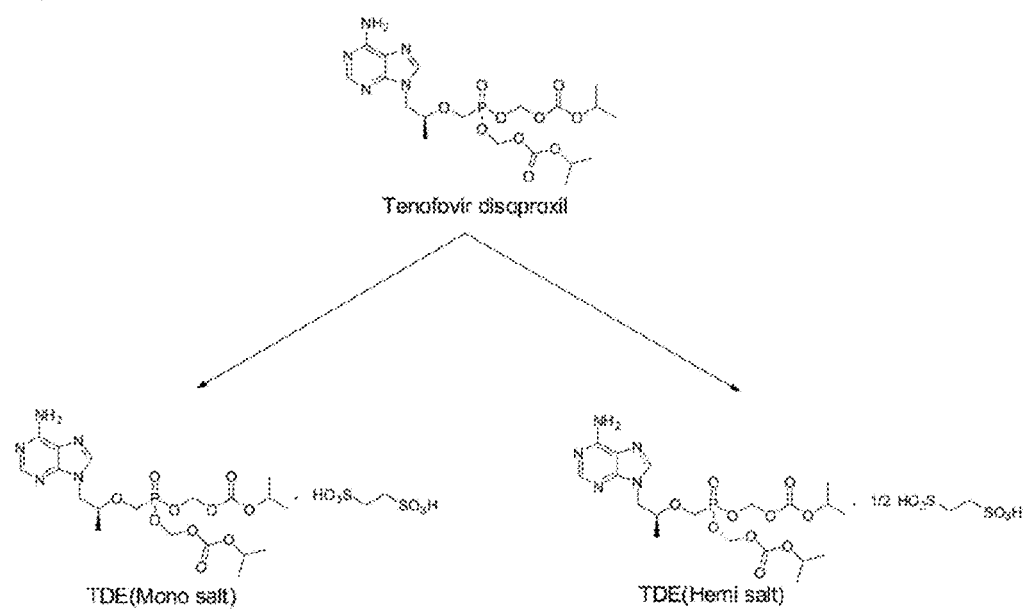
FIG. 1b shows comparison of the structures of tenofovir disoproxil hemi-edisylate according to the present invention and tenofovir disoproxil mono-edisylate.

FIG. 1b shows the structures of tenofovir disoproxil hemi-edisylate according to the present invention and tenofovir disoproxil mono-edisylate.

<Test Example 1> Evaluation of Stability (Stressed Conditions) Depending on Generation of Related Substances (1) Comparison with Tenofovir Disoproxil Fumarate In order to evaluate stability (stressed conditions), according to the ICH guidelines, tenofovir disoproxil edisylate of the present invention (Example 1: TDE) and tenofovir As is apparent from Table 1, the tenofovir disoproxil hemi-edisylate of the present invention was very stable under stressed conditions compared to the disoproxil fumarate. In particular, related substances, which were generated from the tenofovir disoproxil fumarate, were very rarely generated in the tenofovir disoproxil hemi-edisylate of the present invention, from which the tenofovir disoproxil hemi-edisylate of the present invention can be concluded to maintain high purity. Among the related substances appearing in an initial stage, only tenofovir isoproxil monoester was increased in its amount and the other related substances were very rarely increased. Furthermore, tenofovir disoproxil hemi-edisylate contained the main degradation product, that is, tenofovir isoproxil monoester, in an amount of 0.37%, thus considerably improving stability.

(2) Tenofovir Disoproxil Mono-Edisylate

The tenofovir disoproxil hemi-edisylate of the present invention (Example 1: TDE (hemi salt)), serving as a test group, and tenofovir disoproxil mono-edisylate (Comparative Example 2: TDE (mono salt)), serving as a control group, were evaluated for stability for 3 weeks in the same manner as in (1) above. The results are shown in FIG. 1c.

Figure 1C:
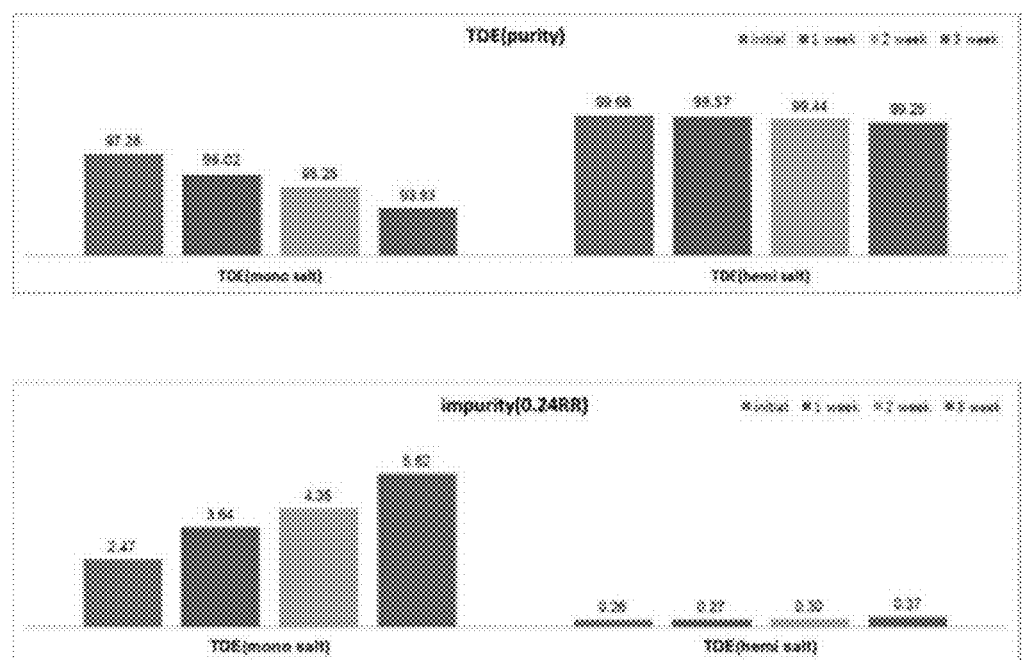
FIG. 1c is graphs showing the results of evaluation of stability of tenofovir disoproxil hemi-edisylate and tenofovir disoproxil mono-edisylate.

As shown in FIG. 1c, the tenofovir disoproxil hemi-edisylate of the present invention was very stable under stressed conditions compared to the tenofovir disoproxil mono-edisylate. In particular, the tenofovir disoproxil hemi-edisylate of the present invention generated almost no related substances over time and thus maintained its high purity, and the related substance was generated in a very small amount of 0.37 at the $3^{rd}$ week, thus exhibiting stability at least 15 times superior to that of tenofovir disoproxil mono-edisylate, in which the related substance of 5.62 was observed in the same period.

Therefore, the tenofovir disoproxil hemi-edisylate of the present invention can be confirmed to be a drug that is able to minimize the generation of related substances to thus enable storage under conditions related to increase in the amounts of the related substances to be facilitated, and also enables long-term storage.

<Test Example 2> Evaluation of Solubility

Solubility is regarded as important in terms of manufacturing drugs. In the case where a drug having high efficacy has low solubility, the development of products may become difficult. If the drug has low solubility, it may be precipitated and thus oral absorption may be significantly decreased.

The saturation solubility of the tenofovir disoproxil hemi-edisylate of the present invention (Example 1) and the tenofovir disoproxil fumarate salt (Comparative Example 1) as a control group were evaluated. The results are shown in Table 2 below.

TABLE 2

| Tenofovir disoproxil | DW (Deionized Water) | pH 1.2 | pH 4.0 | pH 6.8 |
|---|---|---|---|---|
| Fumarate (mg/mL) | 13.5 | 39.2 | 13.2 | 9.4 |
| Hemi-edisylate (mg/mL) | 2200 | 2680 | 2280 | 2400 |

<Test Example 3> Evaluation of Stability Depending on Changes in pH

When a drug is orally administered, it is absorbed in vivo through the stomach, duodenum, small intestine, etc. Hence, stability depending on changes in pH has a great influence on the release rate of a drug. In the present invention, stability was measured using deionized water and three different pH buffer solutions (at pH 1.2, 4.0, and 6.8) for release testing. A test method was performed in a manner in which 5 mg of each of the tenofovir disoproxil hemi-edisylate of the present invention and the tenofovir disoproxil fumarate as a control group was accurately weighed, completely dissolved in 1 mL of a mixture of acetonitrile and water (1:19), and then added with 9 mL of each of the above pH buffer solutions. The individual samples thus prepared were placed in a chamber at 30° C. and changes in the amounts thereof over time were quantified using HPLC.

Figure 2:
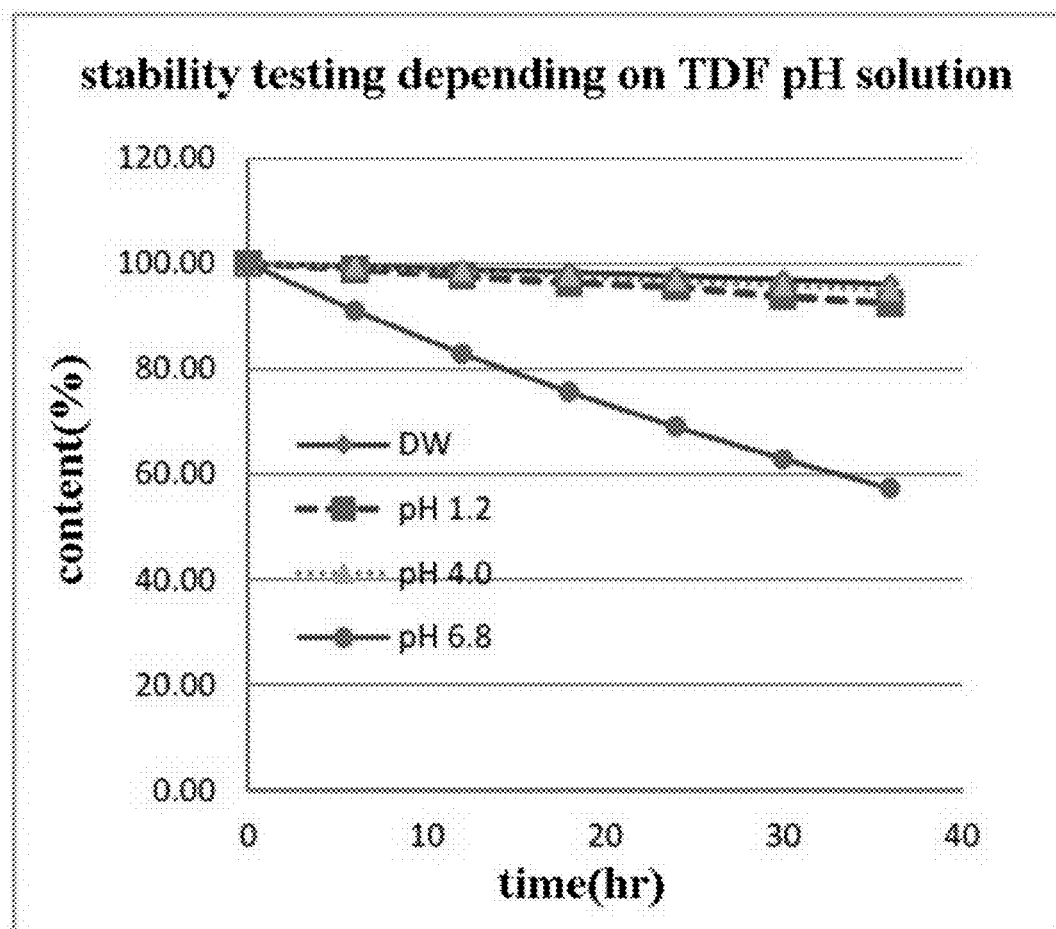
FIG. 2 is a graph showing the results of measurement of stability of tenofovir disoproxil fumarate (TDF, Comparative Example 1) depending on changes in pH.
Figure 3:
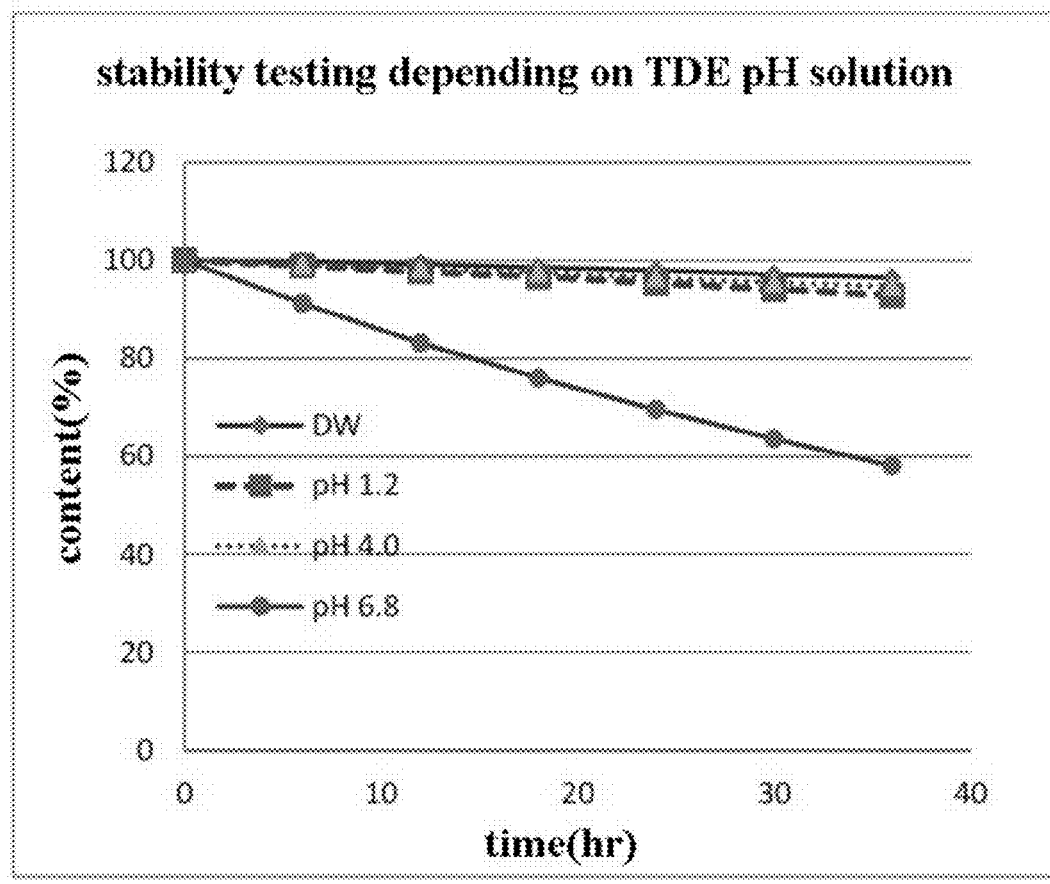
FIG. 3 is a graph showing the results of measurement of stability of tenofovir disoproxil hemi-edisylate (TDE, Example 1) depending on changes in pH.

FIGS. 2 and 3 show the results of stability depending on changes in pH in the tenofovir disoproxil hemi-edisylate (Example 1: TDE) and the tenofovir disoproxil fumarate (Comparative Example 1: TDF). As shown in FIGS. 2 and 3, the tenofovir disoproxil hemi-edisylate of the present invention exhibited stability equal to that of a conventional tenofovir disoproxil fumarate product.

<Test Example 4> PXRD (Powder X-Ray Diffraction, X-Ray Diffraction Analysis)

As for X-ray powder diffraction, the diffraction pattern varies when the crystal structure and the compound form of a material are different. The results thereof are compared with those of a standard material to thus confirm the crystal structure of a material. The tenofovir disoproxil hemi-edisylate of the present invention and the control groups, namely the tenofovir disoproxil fumarate and the tenofovir disoproxil mono-edisylate, were analyzed using a Rigaku MiniFlex 600.

The tenofovir disoproxil hemi-edisylate salt A of the present invention had the X-ray powder diffraction peak values shown in FIG. 5, having those at 4.14°, 10.40°, 11.67°, 12.64°, 12.90°, 13.24°, 15.64°, 16.30°, 16.86°, 18.69°, 18.74°, 19.19°, 19.82°, 20.74°, 21.36°, 21.89°, 22.46°, 23.19°, 23.72°, 24.88°, 25.56°, 26.21°, and 27.04°.

The tenofovir disoproxil hemi-edisylate salt B of the present invention characteristically had the X-ray powder diffraction peak values shown in FIG. 6, having those at 3.32°, 4.18°, 5.13°, 7.31°, 8.59°, 10.01°, 10.42°, 10.97°, 11.56°, 12.64°, 12.95°, 13.25°, 14.67°, 15.53°, 16.39°, 17.33°, 18.15°, 18.75°, 19.28°, 19.93°, 20.44°, 20.81°, 21.37°, 22.03°, 22.49°, 22.84°, 23.28°, 23.75°, 24.66°, 25.00°, 25.65°, 26.36°, 27.1°, 27.76°, 28.16°, 28.79°, 30.31°, and 31.17°. It was found to have crystalline forms different from those of the tenofovir disoproxil fumarate (U.S. Pat. No. 5,935,946) and the tenofovir disoproxil mono-edisylate.

Figure 4A:
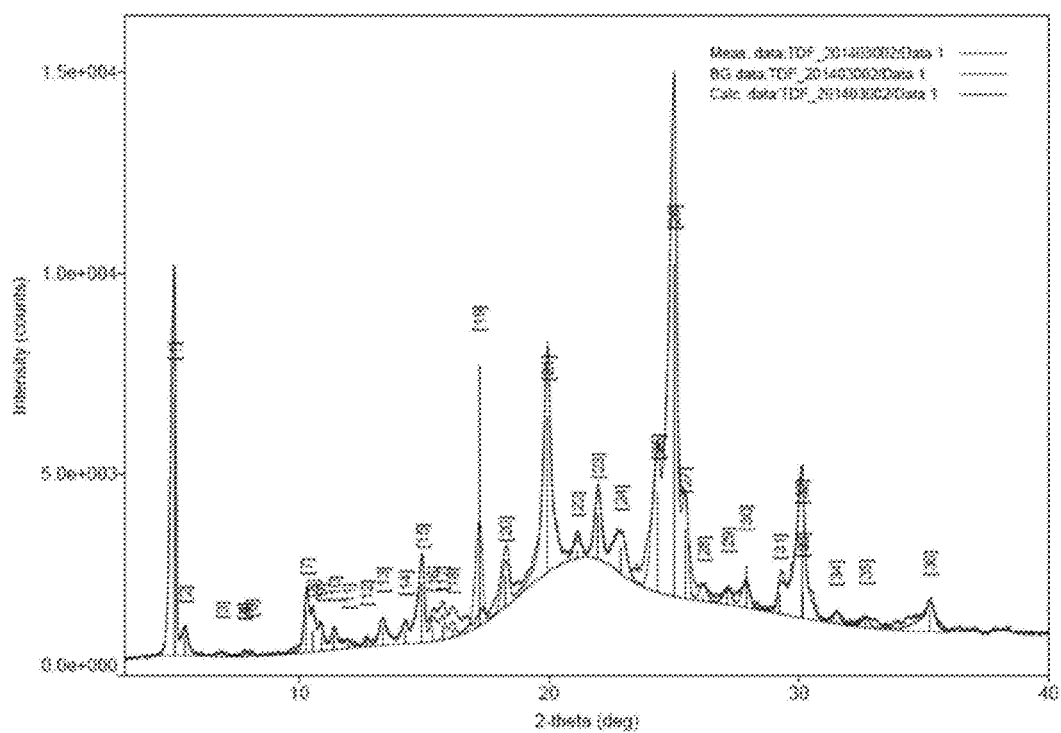
FIG. 4a shows the results of X-ray diffraction analysis of tenofovir disoproxil fumarate.

FIG. 4a shows the results of X-ray diffraction analysis of the tenofovir disoproxil fumarate.

Figure 4B:
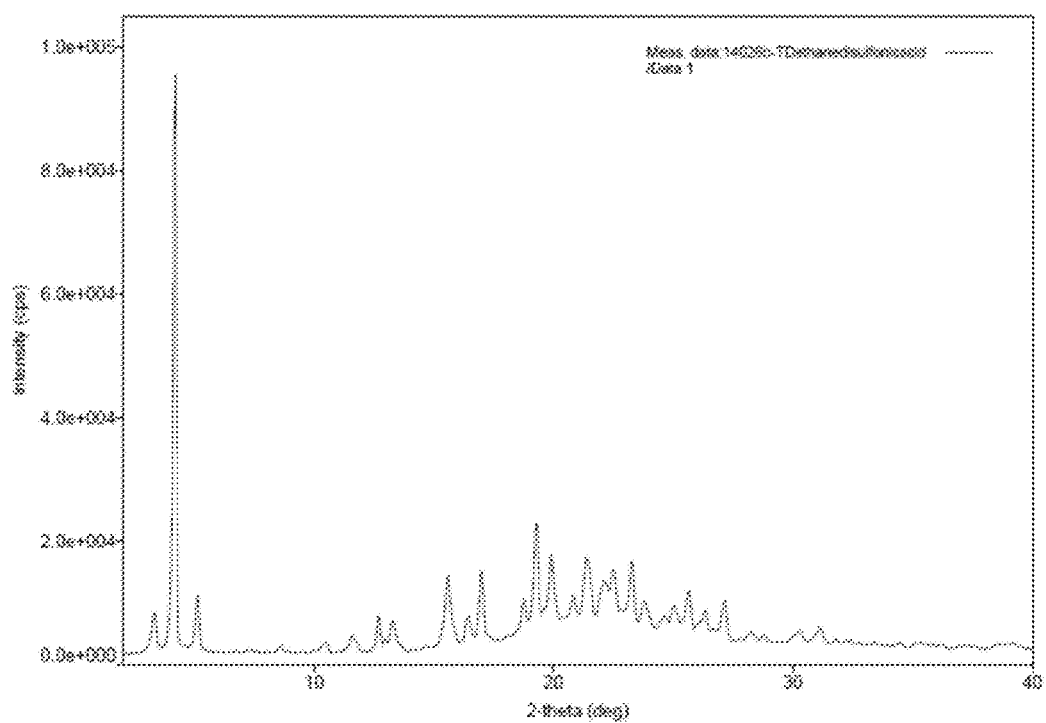
FIG. 4b shows the results of X-ray diffraction analysis of tenofovir disoproxil mono-edisylate.

FIG. 4b shows the results of X-ray diffraction analysis of the tenofovir disoproxil mono-edisylate.

FIG. 5 shows the results of X-ray diffraction analysis of the tenofovir disoproxil hemi-edisylate A.

FIG. 6 shows the results of X-ray diffraction analysis of the tenofovir disoproxil hemi-edisylate B.

<Test Example 5> DSC (Differential Scanning Calorimetry)

Figure 7B:
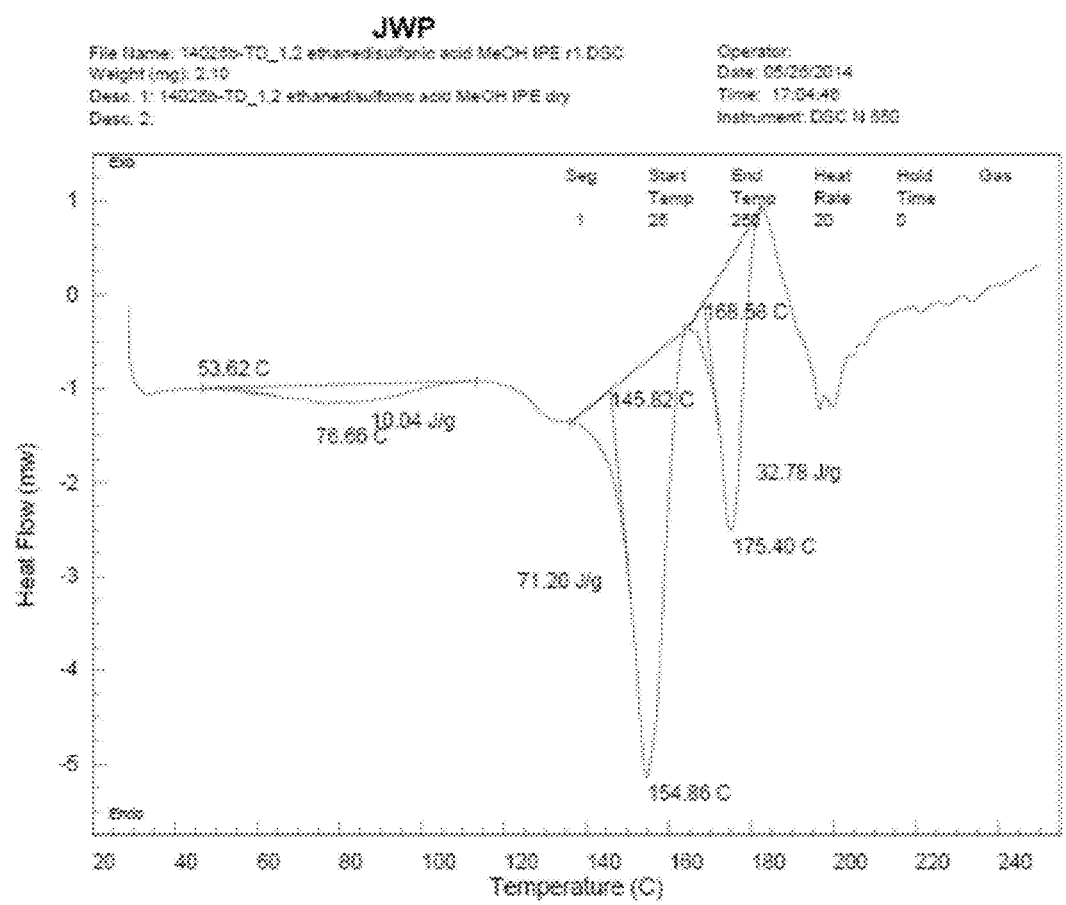
FIG. 7b shows the measurement values of DSC of tenofovir disoproxil mono-edisylate.
Figure 8:
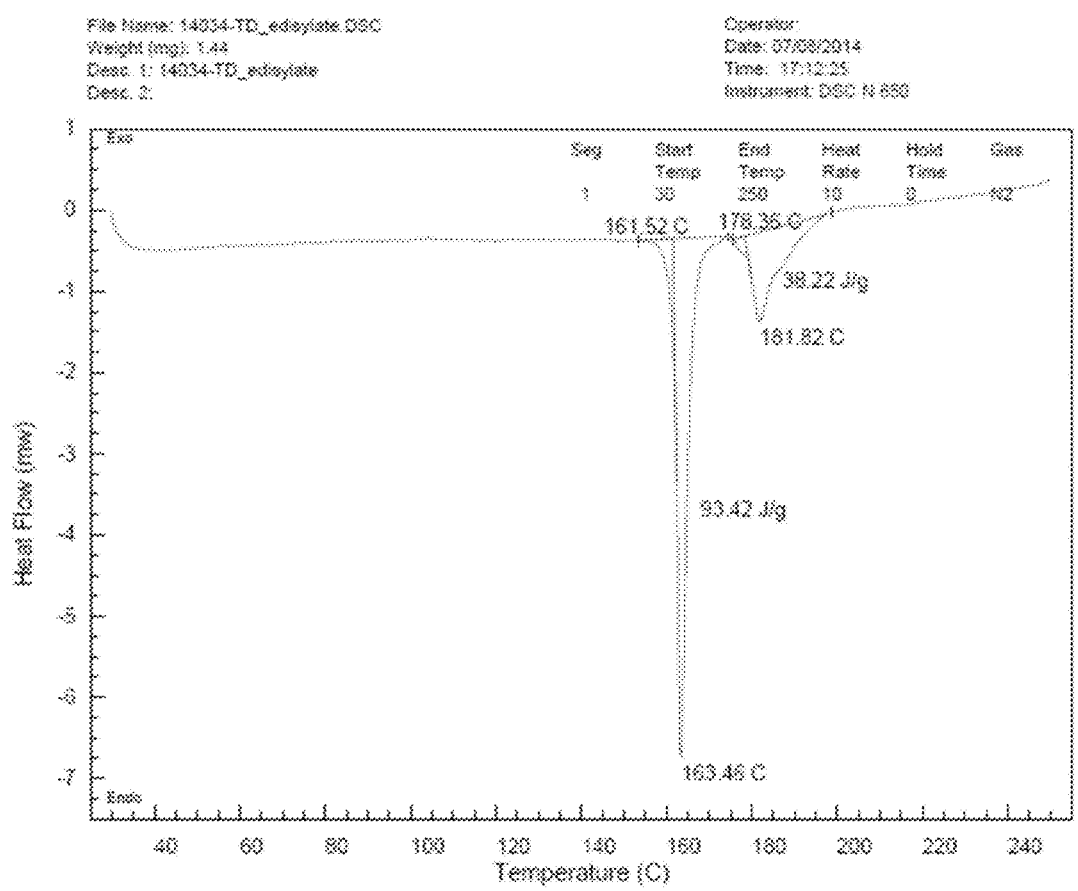
FIG. 8 shows the measurement values of DSC of tenofovir disoproxil hemi-edisylate.

DSC is widely utilized to measure change in heat flow with respect to temperature, associated with heat transfer of a material. The tenofovir disoproxil hemi-edisylate of the present invention and the control groups, namely the tenofovir disoproxil fumarate and the tenofovir disoproxil mono-edisylate, were measured at a heating rate of 20° C./min under nitrogen conditions using SCINCO DSC N650. FIG. 7a shows the measurement values of DSC of the tenofovir disoproxil fumarate, FIG. 7b shows the measurement values of DSC of the tenofovir disoproxil mono-edisylate, and FIG. 8 shows the measurement values of DSC of the tenofovir disoproxil hemi-edisylate.

INDUSTRIAL APPLICABILITY

According to the present invention, tenofovir disoproxil edisylate salt can minimize the generation of related substances over time compared to tenofovir disoproxil fumarate salt, whereby the production of impurities can be significantly decreased during the storage of products containing the salt compound of the invention, thus increasing stability of drugs and obviating the need to perform additional studies on toxic effects.

The invention claimed is:

1. A stable, tenofovir disoproxil edisylate salt, represented by Chemical Formula 1 below

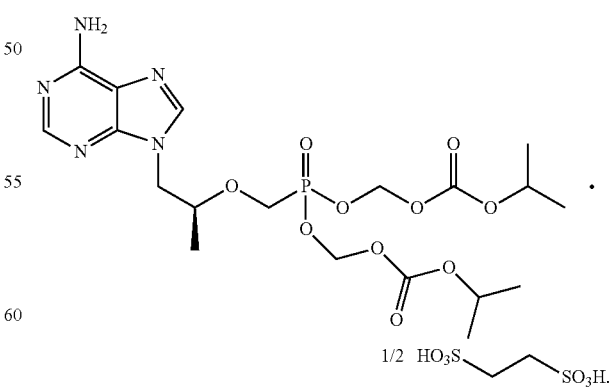

2. The stable, tenofovir disoproxil edisylate salt of claim 1 in crystalline form having X-ray powder diffraction peak values of (i) or (ii) below:

(i) tenofovir disoproxil edisylate A:
4.14°, 10.40°, 11.67°, 12.64°, 12.90°, 13.24°, 15.64°, 16.30°, 16.86°, 18.69°, 18.74°, 19.19°, 19.82°, 20.74°, 21.36°, 21.89°, 22.46°, 23.19°, 23.72°, 24.88°, 25.56°, 26.21°, and 27.04°; or (ii) tenofovir disoproxil edisylate B:
3.32°, 4.18°, 5.13°, 7.31°, 8.59°, 10.01°, 10.42°, 10.97°, 11.56°, 12.64°, 12.95°, 13.25°, 14.67°, 15.53°, 16.39°, 17.33°, 18.15°, 18.75°, 19.28°, 19.93°, 20.44°, 20.81°, 21.37°, 22.03°, 22.49°, 22.84°, 23.28°, 23.75°, 24.66°, 25.00°, 25.65°, 26.36°, 27.1°, 27.76°, 28.16°, 28.79°, 30.31°, and 31.17°.

3. A pharmaceutical composition, comprising a therapeutically effective amount of the tenofovir disoproxil edisylate salt of claim 1 and a pharmaceutically acceptable excipient.

4. The pharmaceutical composition of claim 3, wherein the pharmaceutical composition is provided in a dosage form of a tablet, a capsule, a powder, a granule, a dropping pill, a pulvis, a bolus, a tincture, or a cataplasm.

5. The pharmaceutical composition of claim 3 further comprising a basic pharmaceutical carrier.

6. The pharmaceutical composition of claim 5, wherein the basic pharmaceutical carrier is selected from calcium carbonate, magnetic carbonate, zinc carbonate, ferrous carbonate, aluminum carbonate, magnesium hydroxide, calcium hydroxide, aluminum hydroxide or ferrous hydroxide.

7. A method of preparing a tenofovir disoproxil edisylate salt, comprising reacting tenofovir disoproxil with an edisylate dihydrate.

8. The method of claim 7, characterized in that the tenofovir disoproxil and the edisylate dihydrate are reacted at a molar ratio of 1:0.5 to 1.5.

9. The method of claim 8, characterized in that the tenofovir disoproxil and the edisylate dihydrate are reacted at a molar ratio of 1:0.5 to 0.6.

* * * * *